United States Patent [19]

Gonenne

[11] Patent Number: 5,264,211
[45] Date of Patent: * Nov. 23, 1993

[54] USE OF INTRATRACHEAL ADMINISTRATION OF SOD TO PROTECT HUMANS FROM LUNG INJURY DUE TO HYPEROXIA AND HYPERVENTILATION

[75] Inventor: Amnon Gonenne, Great Neck, N.Y.

[73] Assignee: Bio-Technology General Corp., N.Y.

[*] Notice: The portion of the term of this patent subsequent to May 26, 2009 has been disclaimed.

[21] Appl. No.: 864,627

[22] Filed: Apr. 7, 1992

Related U.S. Application Data

[63] Continuation of Ser. No. 692,630, Apr. 29, 1991, Pat. No. 5,116,616.

[51] Int. Cl.$^5$ .............................................. A61K 37/50
[52] U.S. Cl. .................................... 424/94.4; 424/94.1
[58] Field of Search ............................. 424/94.4, 94.1

[56] References Cited

U.S. PATENT DOCUMENTS 4,742,004  5/1988  Hartman et al. ...................... 435/70

OTHER PUBLICATIONS

Crapo, et al., *Amer. Rev. Respir. Disease* (1977); 115:1027–1033.
Seo, S. C., et al., *Chung-Ang J. of Medicine* (1987); 12(2):259–271.
Padmanabhan, R. V., et al., *Am. Rev. Respir. Disease* (1985); 132:164–167.
Turrens, J. F. et al., *J. Clin. Invest.* (1984); 73:87–95.
Crapo, et al., *Amer. Rev. Respir. Disease* (1980); 122:123–143.
Walther, F. J., et al., *J. Free Radicals in Biol & Med.* (1986); 2:289–293.
Davis, Jonathan J., et al., *J. Amer. Physiology (1989); 67:1007–1012.*

*Primary Examiner*—Douglas W. Robinson
*Assistant Examiner*—Jean C. Witz
*Attorney, Agent, or Firm*—John P. White

[57] ABSTRACT

The subject invention provides a method of protecting a human from lung injury due to hyperoxia and hyperventilation which comprises intratracheally administering to the human an amount of free CuZnSOD effective to protect the human from lung injury due to hyperoxia and hyperventilation.

10 Claims, 5 Drawing Sheets

USE OF INTRATRACHEAL ADMINISTRATION OF SOD TO PROTECT HUMANS FROM LUNG INJURY DUE TO HYPEROXIA AND HYPERVENTILATION

This is a continuation of application Ser. No. 692,630, filed Apr. 29, 1991, now U.S. Pat. No. 5,116,616.

BACKGROUND OF THE INVENTION

Throughout this specification, various publications are referenced by Arabic numerals within parentheses. Full citations for these references may be found at the end of the specification immediately preceding the claims. The disclosures of these publications in their entireties are hereby incorporated by reference in this specification in order to more fully describe the state of the art to which this invention pertains.

Newborn infants with a variety of respiratory disorders are treated with positive pressure mechanical ventilation and oxygen therapy. This treatment is therapeutic, but can initiate a potent inflammatory response leading to acute lung injury and subsequent Bronchopulmonary Dysplasia or BPD. BPD begins as an acute lung injury that initiates a series of inflammatory responses which then evolve into chronic lung disease. The exact mechanisras responsible for pathophysiologic disruption to the lung in infants with BPD are not completely understood. One possibility is that oxidative insult caused by superoxide radicals is responsible for the initial, acute lung injury which ultimately leads to the development of BPD. If acute lung injury could be ameliorated, then it may be possible to prevent BPD.

Superoxide is a highly toxic free radical that may be an important component of pulmonary oxygen toxicity (1). SOD facilitates the conversion of superoxide radicals ($O_2^-$) to hydrogen peroxide ($H_2O_2$). However, Crapo et al. found that free superoxide dismutase, administered by intraperitoneal injection or by aerosolization, failed to modify either the time course or the cumulative toxicity of 100% oxygen in adult rats (1).

Other experiments have been performed using free and liposome entrapped superoxide dismutase to determine the effect on pulmonary oxygen toxicity in rats (2,3). Seo et al. observed the effect of intratracheally administered free and liposome entrapped bovine superoxide dismutase and catalase by measuring the enzyme activity, oxygen radicals, pulmonary hemorrhage and survival rate after exposure to hyperoxia in adult rats (2). Free superoxide dismutase delivered to adult rats intratracheally with catalase had no protective effect against hyperoxia lung damage, while the intratracheally-administered liposome-entrapped superoxide dismutase and catalase enhanced the activity of total superoxide dismutase, Mn-superoxide dismutase and catalase in the rats (2). PadrAanabhan et al. found that prior intratracheal adrainistration of liposome-encapsulated bovine CuZn-superoxide dismutase produced a significant increase in the activities of these enzymes in the lung tissue of rats exposed to hyperoxic levels of oxygen compared with that in control animals under the same conditions with free superoxide dismutase (3).

As demonstrated by the references discussed above (1-3), until now, attempts to protect animals from lethal effects of pure oxygen by intratracheal administration of free superoxide dismutase have been unsuccessful. The subject invention provides a method for intratracheally administering free human CuZn superoxide dismutase to protect humans from lung damage due to hyperoxia and hyperventilation.

SUMMARY OF THE INVENTION

The subject invention provides a method of protecting a human from lung injury due to hyperoxia and hyperventilation which comprises intratracheally administering to the human an amount of free CuZnSOD effective to protect the human from lung injury due to hyperoxia and hyperventilation.

DETAILED DESCRIPTION OF THE INVENTION

The subject invention provides a method of protecting a human from lung injury, particularly lung injury due to hyperoxia and hyperventilation, which comprises intratracheally administering to the human an amount of free CuZnSOD effective to protect the human from such lung injury.

In one embodiment of the method, the human is an adult; in another, the human is a neonate; and in a further embodiment, the neonate is premature. In practicing the method of this invention, a surfactant may desirably be administered prior to administering the free CuZnSOD to the premature neonate.

As used herein "CuZnSOD" means a polypeptide having an amino acid sequence identicial, or substantially identical, to the amino acid sequence of a naturally-occurring CuZnSOD, whether of human, bovine or other mammalian origin, and having the biological activity of such naturally-occurring CuZnSOD. Thus, CuZnSOD encompasses polypeptides whose amino acid sequence varies from that of the naturally occurring CuZnSOD by one or more amino acid, either internally such as a point mutation, or by addition or deletion at the COOH− terminus or NH2− terminus or both, provided that the biological activity is unchanged.

In the presently preferred embodiment of the invention the CuZnSOD is a nonacetylated, nonglycosylated polypeptide analog of human CuZnSOD prepared in *E. coli* (see U.S. Pat. No. 4,742,004, the disclosure of which is hereby incorporated by reference into the present application). As used herein, "free CuZnSOD" means CuZnSOD which is neither encapsulated nor bound to another polymer such as polyethylene glycol (PEG) or another Polypeptide such as albumin.

The amount of CuZnSOD intratracheally administered may vary from about 0.5 mg/kg to about 50 mg/kg of body weight of the human being treated. Preferably, the amount is from about 5 mg/kg to about 10 mg/kg, for example about 5 mg/kg body weight of the human being treated. The intratracheal free CuZnSOD may be administered in any other of the methods well known to those skilled in the art. For example, the CuZnSOD may be administered in the form of an aerosol or may be administered by instillation. If administered in the form of an aerosol, a nebulizer is used to produce CuZnSOD in aerosol form.

Typically, the free CuZnSOD is administered in a pharmaceutically acceptable carrier, for example a saline solution. Such carriers are well known in the art and the specific carriers employed may be varied depending upon factors such as size of the subject being treated, treatment dose and the like.

Further, the time over which the CuZnSOD is administered may vary as is well known in the art to achieve the desired results, for example, the free CuZnSOD may be administered as an aerosol for from about 30 minutes to about 3 hours per treatment regimen (e.g. one daily).

In addition, forms of SOD other than CuZnSOD may be substituted for CuZnSOD in the method of this invention, such as MnSOD, extracellular SOD or analogs thereof. If MnSOD is substituted for CuZnSOD, the preferred amount of MnSOD intratracheally administered to the human is from about 0.1 mg/kg to about 50 mg/kg of body weight of the human.

As used herein "MNSOD" means a polypeptide having an amino acid sequence identicial, or substantially identical, to the amino acid sequence of a naturally-occurring MNSOD, whether of human, bovine or other mammalian origin, and having the biological activity of such naturally-occurring MNSOD. Thus, MNSOD encompasses polypeptides whose amino acid sequence varies from that of the naturally occurring MNSOD by one or more amino acid, either internally such as a point mutation, or by addition or deletion at the COOH− terminus or NH2− terminus or both, provided that the biological activity is unchanged.

EXPERIMENTAL DETAILS

The subject invention involves the acute response of the lung to injury caused by oxygen and mechanical ventilation and demonstrates that prophylactic superoxide dismutase (SOD) could prevent this injury.

A multidisciplinary approach was used to study the biochemical, cellular, biophysical, physiologic, and pathologic effects of oxygen and mechanical ventilation on the newborn lung. The neonatal piglet has been chosen as the model for these experiments. The piglet is large enough at tern for ventilation and for the study of physiologic variables. The lung of the newborn piglet is similar physiologically and morphologically to that of a preterm human infant. Anti-oxidant enzyme activity of the newborn piglet is also comparable to that of a preterm human infant.

The piglet model of the subject invention is a better model than the previously used rat model for humans for these experiments because rats, unlike humans, can be induced to survive in a 100% $O_2$ environment (2,4,5). In Walther et al. (6), the first experiment performed using premature animals instead of rats, polyethylene glycol (PEG) superoxide dismutase was delivered with PEG-catalase intravenously to premature lambs, which resulted in decreased lung damage during subsequent mechanical ventilation (6). However, although lambs are a better model for humans than are rats, the subject invention differs from the experiment with premature lambs because the superoxide dismutase used in the subject invention is free CuZn superoxide dismutase, not derivatized PEG-SOD, is delivered alone, not in cozabination with PEG-CAT, and is delivered intratracheally, not intratravenously, to neonatal piglets.

In newborn piglets, 48 hours of hyperoxia and hyperventilation causes acute lung injury as evidenced by biochemical, cellular and pathophysiologic changes in the lung (7). This experiment demonstrates that prophylactic superoxide dismutase (SOD) prevents such lung injury to newborn piglets.

To determine if prophylactic SOD would prevent acute lung injury caused by hyperoxia and hyperventilation, 24 piglets (1.3±0.3 kg, 1–2 days old) were studied. Ten piglets were hyperventilated ($PaCO_2$ 15–20 torr) with 100% $O_2$ for 48 h (group I, pos. control) and compared to 8 identically treated piglets given a single intratracheal dose of SOD (5 mg/kg in saline) at time zero (group II). Six piglets were normally ventilated ($PaCO_2$ 40–45 torr) with 21% $O_2$ (group III, neg. control). Pulmonary function and tracheal aspirates were examined at 0, 24, and 48 h. Morphologic and surfactant(s) analyses were performed at the conclusion of the study. In group I, there was a significant decrease in lung compliance and an increase in tracheal aspirate cell counts, number of neutrophils (PMNs), PMN chemotactic activity, elastase activity and albumin and total protein concentrations over 48 h. Morphologic examination revealed patchy, moderate atelectasis, edema, inflammation and cell necrosis. In contrast the only significant change in group II was aspirate total protein concentration. Changes in cellular, biochemical and lung morphologic variables in group II were significantly less than group I and comparable to group III controls. Serum SOD levels peaked at 0.6±0.2 μg/ml at 12 h and were 0.2±0.05 μg/ml at 48 h. Lung tissue SOD was 8.5±3.6 μg SOD/mg protein at 48 h. S was active in all groups. When SOD was added directly to tracheal aspirates from group I (0.5, 5, 50 μg/ml), no effect on PMN chemotaxis was noted, suggesting SOD had no direct effect on PMNS, but prevented PMN recruitment by decreasing the production of chemotactic mediators. Results indicate that acute lung damage from 48 h of hyperoxia and hyperventilation can be significantly ameliorated by a single prophylactic dose of intratracheal SOD.

MATERIALS AND METHODS

Study Protocol 24 newborn piglets, 1.3±0.3 kg (1-2 days old)

Group I, positive control—10 hyperventilated for 48 hours ($PaCO_2$ 15-20 torr), $FiO_2$ 1.0, (baseline, 24 h, 48 h studies).

Group II—8 treated as above, but given a single IT dose of recombinant human Cu/Zn SOD (5 mg/kg in saline).

Group III, negative control—6 normally ventilated for 48 hours ($PaCO_2$ 35-45 torr), $FiO_2$ 0.21.

Tracheal Aspirates

Figure 1:
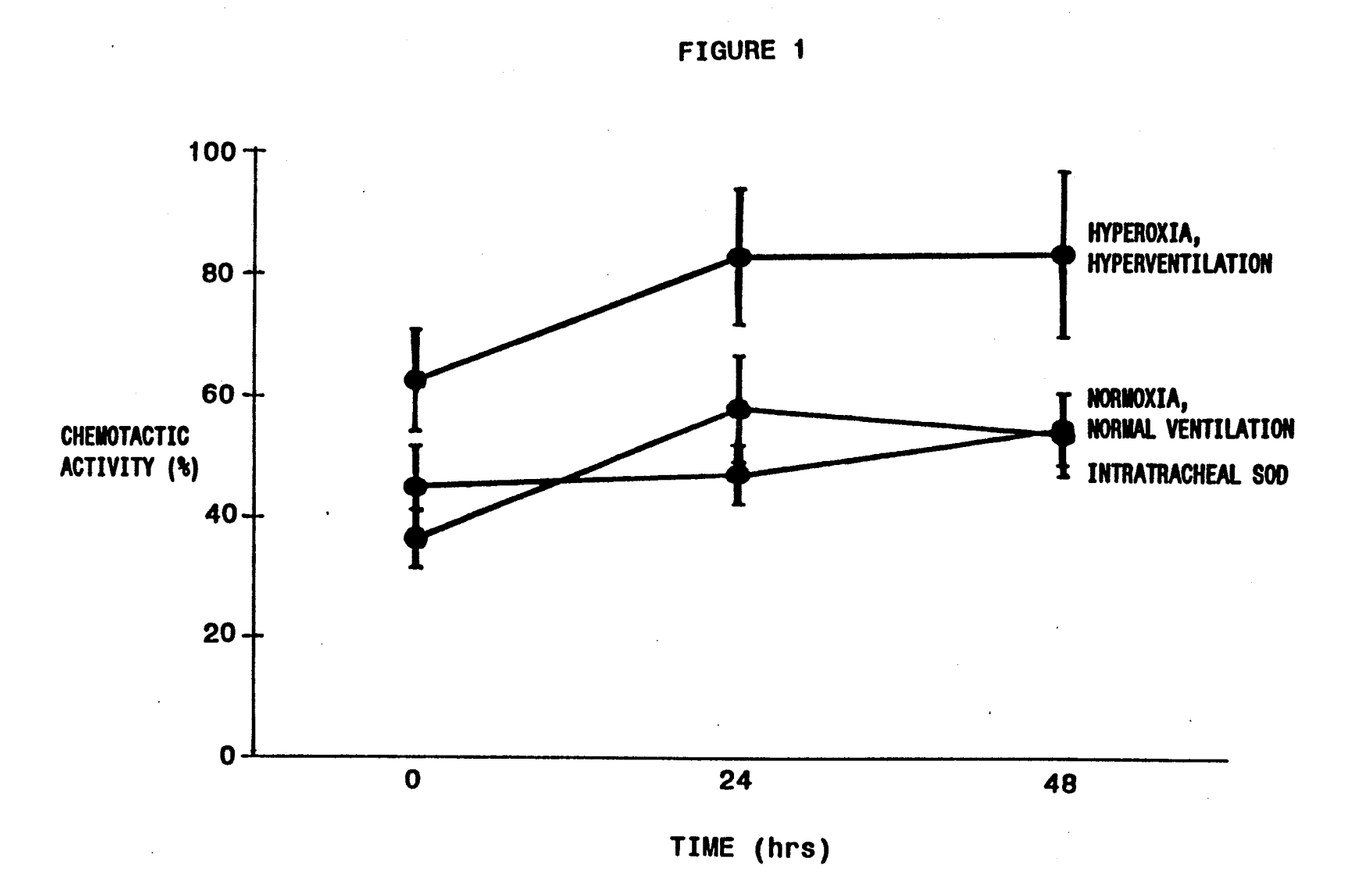
FIG. 1: Percent polymorphonuclear (PMN) chemotactic activity in the neonatal piglet of group I (hyperventilated and hyperoxygenated piglets); group II (hyperventilated and hyperoxygenated piglets given a single intratracheal dose of superoxide dismutase at time zero); and group III (normally ventilated piglets, under normoxia conditions, negative control group).
Figure 2A:
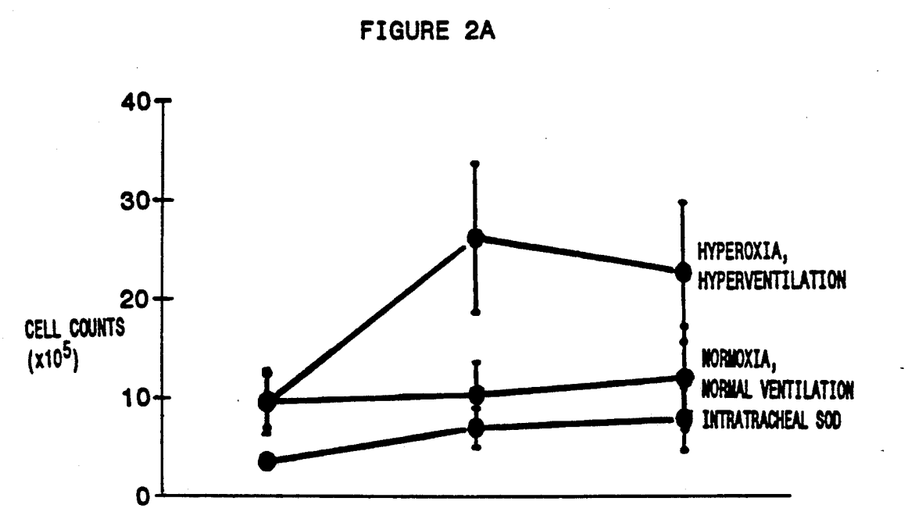
FIGS. 2A and 2B: Tracheal aspirate cell counts and number of PMNs in the neonatal piglet of group I (hyperventilated and hyperoxygenated piglets); group II (hyperventilated and hyperoxygenated piglets given a single intratracheal dose of superoxide dismutase at time zero); and group III (normally ventilated piglets, under normoxia conditions, negative control group).
Figure 2B:
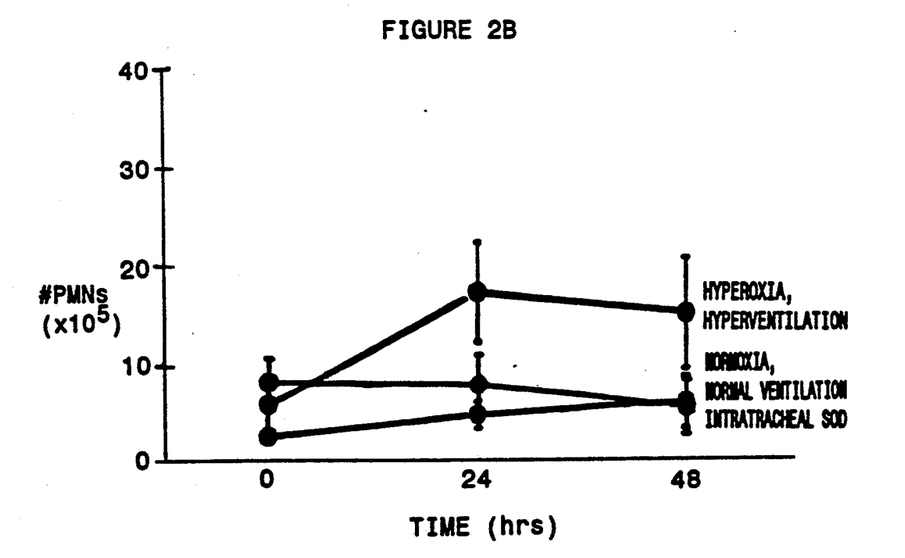
Figure 3A:
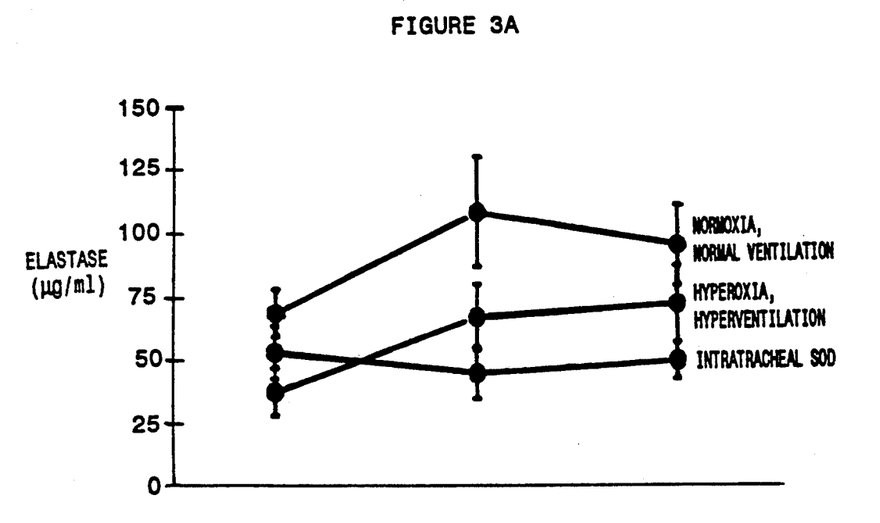
FIGS. 3A and 3B: Elastase activity and albumin in the neonatal piglet of group I (hyperventilated and hyperoxygenated piglets); group II (hyperventilated and hyperoxygenated piglets given a single intratracheal dose of superoxide dismutase at time zero); and group III (normally ventilated piglets, under normoxia conditions, negative control group).
Figure 3B:
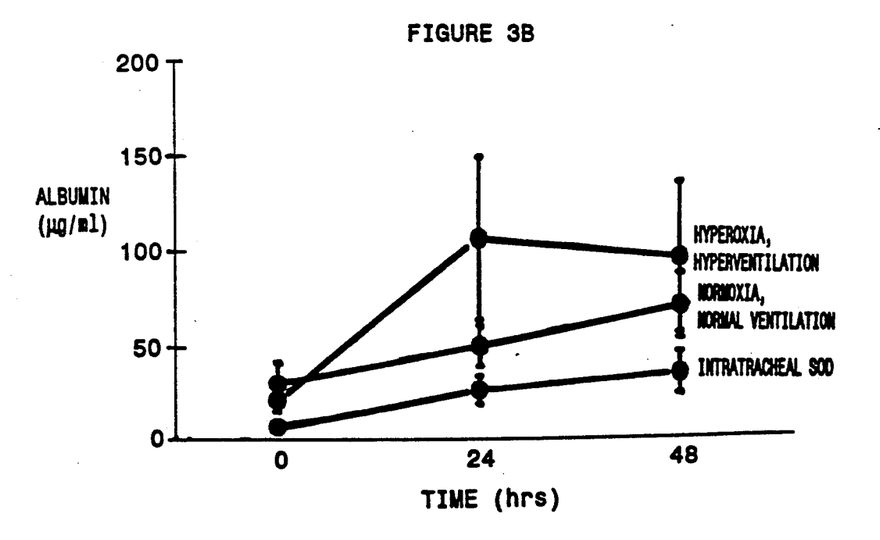
Figure 5:
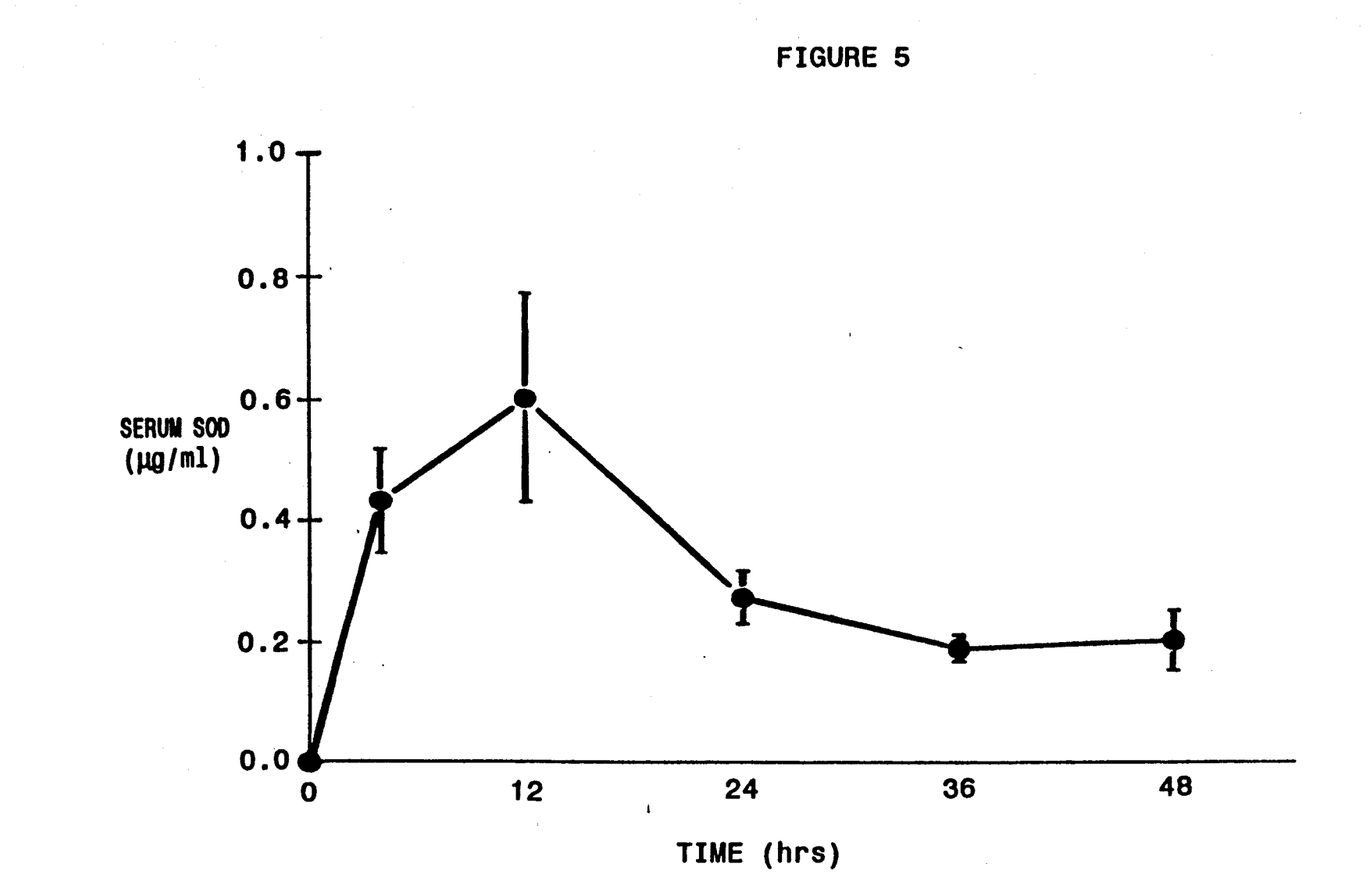
FIG. 5: Concentration of superoxide dismutase in the serum of the neonatal piglet of group I (hyperventilated and hyperoxygenated piglets); group II (hyperventilated and hyperoxygenated piglets given a single intratracheal dose of superoxide dismutase at time zero); and group III (normally ventilated piglets, under normoxia conditions, negative control group).

PMN chemotactic activity of Groups I, II and III (FIG. 1). Cell counts and differentials of Groups I, II and III (FIGS. 2A and 2B). Elastase (FIGS. 3A and 3B). Albumin (FIG. 3). Total protein concentration (FIG. 5).

Pulmonary Function Tests

Figure 4:
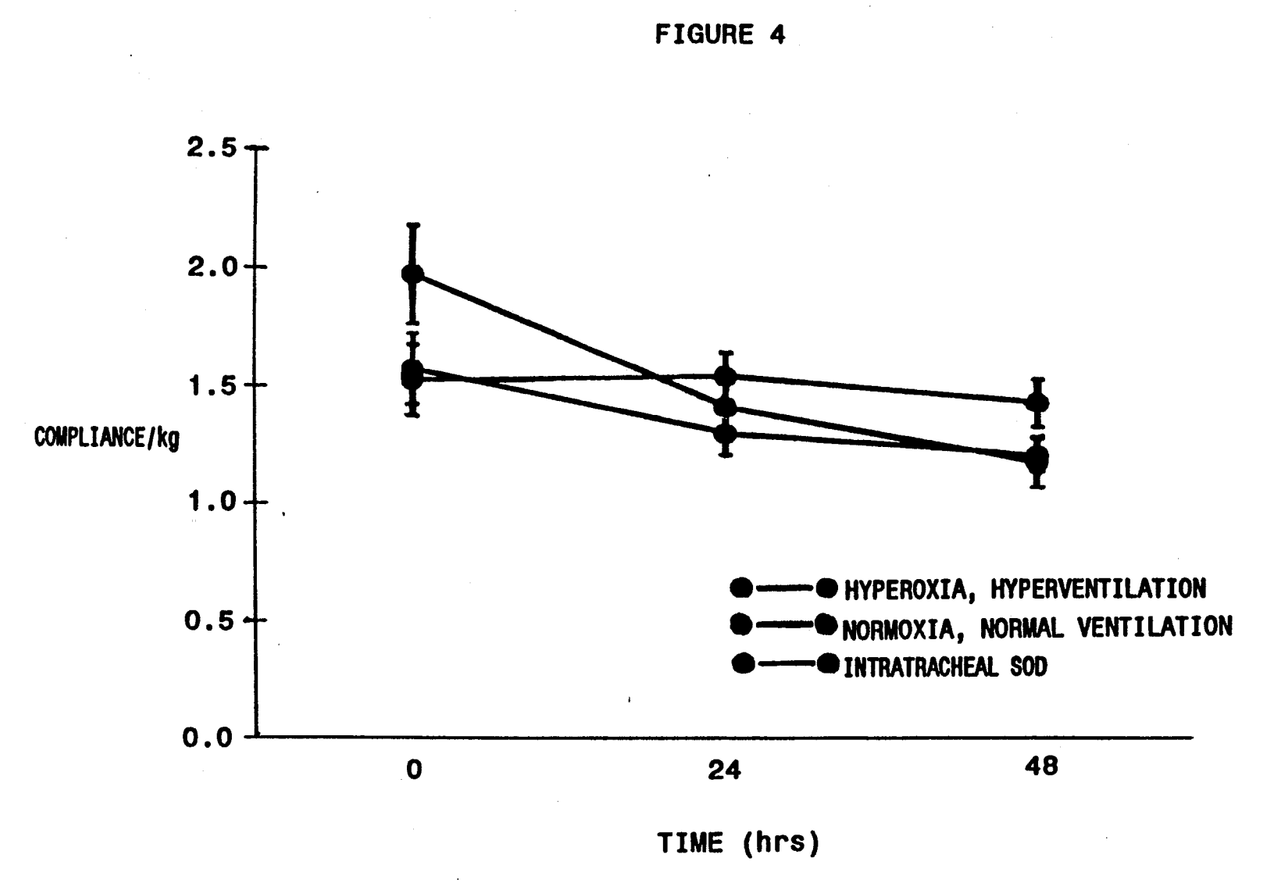
FIG. 4: Lung compliance per kg in the neonatal piglet of group I (hyperventilated and hyperoxygenated piglets); group II (hyperventilated and hyperoxygenated piglets given a single intratracheal dose of superoxide dismutase at time zero); and group III (normally ventilated piglets, under normoxia conditions, negative control group).

Lung compliance (FIG. 4).

Bronchoalveolar Lavage

Quantitative and qualitative surfactant analysis: No negative effect on the integrity of surfactant from administration of superoxide dismutase was observed. Lung compliance improved with surfactant in lung. Furthermore, no negative effect of surfactant on the integrity of superoxide dismutase was observed.

Pathologic Examination

Light microscopy as well as scanning and transmission electron microscopy was used to study the pathologic effects of oxygen and mechanical ventilation on the newborn piglets.

Conclusions

SOD facilitates the conversion of superoxide radicals ($O_2^-$) to hydrogen peroxide ($H_2O_2$). With fewer toxic oxygen radicals present, cell damage is minimized, chemotactic agents for PMNs are not produced, and acute lung injury is reduced.

Hyperoxia and hyperventilation for 48 hours causes significant cellular, biochemical and pathophysiologic changes in the lung. SOD moderated the development of acute lung injury as evidenced by decreased PMN infiltration, elastase activity, protein influx and pathophysiologic abnormalities. Despite increases in protein influx, pulmonary surfactant remained active, and therefore SOD does not adversely affect the activity of pulmonary surfactant.

References

1. Crapo et al., The Failure of Aerosolized Superoxide Dismutase to Modify Pulmonary Oxygen Toxicity, American Review of Respiratory Disease 115:1027-1033).
2. Seo, S. C. et al., The Effect of Intratracheally Administered Free and Liposome Entrapped Superoxide Dismutase and Catalase on Experimentally Exposed Hyperoxic Injury in Rats' Lungs, Chung-Ang Journal of Medicine 12(2):259-271 (June 1987).
3. Padmanabhan, R. V. et al., Protection Against Pulmonary Oxygen Toxicity in Rats by the Intratracheal Administration of Liposome-Encapsulated Superoxide Dismutase or Catalase[1-3], Am. Rev. Respir. Dis. 132:164-167 (1985).
4. Turrens, J. F. et al., Protection Against oxygen Toxicity by Intravenous Injection of Liposome-Entrapped Catalase and Superoxide Dismutase, J. Clin. Invest. 73:87-95 (Jan. 1984).
5. Crapo et al., Structural and Biochemical Changes in Rat Lungs Occurring During Exposures to Lethal and Adaptive Dones of Oxygen, American Review of Respiratory Disease, 122:123-143 (1980).
6. Walther, F. J. et al., Prevention of Oxygen Toxicity with Superoxide Dismutase and Catalase in Premature Lambs, Journal of Free Radicals in Biology & Medicine 2:289-293 (1986).
7. A. M. Gonenne et al., JAP 67:1007-1042 (1989).

What is claimed is:

1. A method of protecting a human from lung injury due to hyperoxia and hyperventilation which comprises intratracheally administering to the human an amount of free NmSOD effective to protect the human from lung injury due to hyperoxia and hyperventilation.
2. A method of claim 1, wherein the free MnSOD is administered in the form of an aerosol.
3. A method of claim 1, wherein the intratracheal administration of free MnSOD is performed by instillation.
4. A method of claim 1, wherein the human is an adult.
5. A method of claim 1, wherein the human is a neonate.
6. A method of claim 5, wherein the neonate is premature.
7. A method of claim 6, wherein a surfactant is administered prior to administering the free MnSOD.
8. A method of claim 1, wherein the amount of free MnSOD is from about 0.5 mg/kg to about 50 mg/kg of body weight of the human.
9. A method of claim 1, wherein the MnSOD is recombinant free MnSOD.
10. A method of claim 1, wherein the free MnSOD is human MnSOD.

* * * * *

UNITED STATES PATENT AND TRADEMARK OFFICE
CERTIFICATE OF CORRECTION

PATENT NO. : 5,264,211
DATED : November 23, 1993
INVENTOR(S) : Amnon Gonenne

It is certified that error appears in the above-indentified patent and that said Letters Patent is hereby corrected as shown below:

Column 1, line 27, "exact mechanisras responsible" should read --exact mechanisms responsible--.

Column 1, line 56, "PadrAanabham et al." should read --Padmanabhan et al.--.

Column 2, line 64, "having-an" should read --having an--.

Column 3, line 15, "Polypeptide" should read --polypeptide--.

Column 3, line 47, "MNSOD" should read --"MnSOD"--.

Column 3, line 50, "MNSOD" should read --MnSOD--.

Column 3, line 52, "naturally-occurring MNSOD. Thus MNSOD" should read --naturally-occurring MnSOD. Thus MnSOD--.

Column 3, line 54, "MNSOD" should read --MnSOD--.

Column 4, line 24, "cozabination" should read --combination--.

UNITED STATES PATENT AND TRADEMARK OFFICE
CERTIFICATE OF CORRECTION

PATENT NO. : 5,264,211

DATED : November 23, 1993

INVENTOR(S) : Amnon Gonenne

It is certified that error appears in the above-indentified patent and that said Letters Patent is hereby corrected as shown below:

Column 5, line 10, "recombinant huinan" should read --recombinant human--.

Column 6, line 32, Claim 1, "NmSOD" should read --MnSOD--.

Signed and Sealed this

Thirty-first Day of October 1995

Attest:

BRUCE LEHMAN

Attesting Officer

Commissioner of Patents and Trademarks